United States Patent [19]

Flynn et al.

[11] Patent Number: 4,837,354

[45] Date of Patent: Jun. 6, 1989

[54] PROCESS FOR MAKING AND ISOLATING (R)-2-HYDROXY-4-PHENYLBUTYRIC ACID AND ESTERS

[75] Inventors: Gary A. Flynn; Douglas W. Beight, both of Cincinnati, Ohio

[73] Assignee: Merrell Dow Pharmaceuticals Inc., Cincinnati, Ohio

[21] Appl. No.: 96,312

[22] Filed: Sep. 9, 1987

Related U.S. Application Data

[63] Continuation of Ser. No. 19,102, Feb. 26, 1987, abandoned.

[51] Int. Cl.$^4$ ............................................. C07C 69/76
[52] U.S. Cl. ...................................... 560/60; 562/470
[58] Field of Search ......................... 560/60; 562/470

[56] References Cited

U.S. PATENT DOCUMENTS 4,374,829  2/1983  Harris et al. ..................... 424/177
4,415,496 11/1983  Harris et al. ..................... 260/239

FOREIGN PATENT DOCUMENTS

EP57998  8/1982  European Pat. Off. .
EP61187  9/1982  European Pat. Off. .
85/7527  5/1986  South Africa .

OTHER PUBLICATIONS

Ohno, A. et al., Bull. Chem. Soc. Jpn, 59(9) 2905-6, 1986.
Fusco, R., J. O. Chem., 49(23) 4374-8, 1984.

*Primary Examiner*—Paul J. Killos
*Attorney, Agent, or Firm*—Louis J. Wille

[57] ABSTRACT

Disclosed herein is a novel compound, (L)-menthyl 2-oxo-4-phenylbutyrate, and an improved process for making and isolating a substantially pure compound of the structural formula:

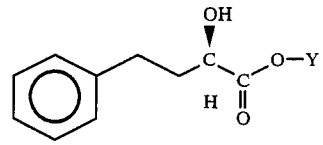

wherein Y is hydrogen or (L)-menthyl the improvement which comprises:
(a) stereoselectively reducing (L)-menthyl 2-oxo-4-phenylbutyrate by contacting said compound with S-B-(3-pinanyl)-9 horabicyclo[3,3,1]nonone,
(b) stereoselectively isolating (L)-menthyl-(R)-2-hydroxy-4-phenylbutyrate by crystallization, and optionally hydrolyzing the so obtained ester;

and further comprises optionally esterifying the so obtained acid by contacting said acid with a $C_1$–$C_6$ alkanol in presence of acid.

9 Claims, No Drawings

PROCESS FOR MAKING AND ISOLATING (R)-2-HYDROXY-4-PHENYLBUTYRIC ACID AND ESTERS

CROSS REFERENCE TO RELATED APPLICATION

This is a continuation of application Ser. No. 019,102, filed Feb. 26, 1987, now abandoned.

Recent advances in medical science have produced compounds which have been shown to be potent inhibitors of Angiotensin-Converting-Enzyme (ACE) and to be useful in the treatment of hypertension in humans. Many of these compounds, such as enalapril, ramipril, cilazapril, quinapril and lysinapril share a common general structural feature which has been found to contribute to enhanced end-use characteristics. The feature common to such compounds is the (S) enantiomer of the moiety 2-amino-4-phenylbutyric acid, or esters thereof, having the structural formula (1)

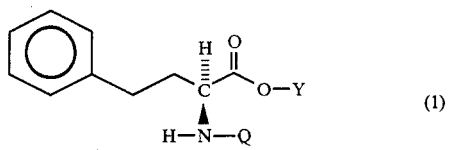

wherein Y is hydrogen or a ($C_1$–$C_6$) alkyl, and Q is the remaining portion of the desired ACE inhibitor. The corresponding enantiomers having the (R)-configuration about the chiral center consisting of the 2-carbon of the butyrate moiety have been shown to lack similar potency as ACE inhibitors and antihypertensive agents and are considerably less desirable in their end-use application.

ACE inhibitors of the structural formula (I) can be prepared by reacting an approprite ester of (R)-2-hydroxy-4-phenylbutyric acid with an appropriate amine under standard conditions well known in the art which are calculated to effect a straight forward $S_N2$ displacement of the 2-hydroxy group by the amine. Such reaction conditions are exemplified in a publication by Urbach and Henning (Tetrahedran Lett. 25, 1143 (1984)) wherein the trifluoromethanesulfonic ester of ethyl (R)-2-hydroxy-4-phenylbutyrate is the reactant in this synthesis. It is therefore desirable to have a method of making and isolating ethyl (R)-2-hydroxy-4-phenylbutyrate and similar compounds for use as intermediates in the synthesis of the various ACE inhibitors.

Most available synthetic approaches for these alkyl esters of (R)-2-hyroxy-4-phenylbutyric acid produce racemic mixtures with the (R)- and (S)-enantiomers present in essentially equal amounts. Procedures required for resolution for the (R) enantiomer have proven to be difficult and time consuming. For example, D. Biquard utilized the (L)-menthyl esters of (R) (S)-2-hydroxy-4-phenylbutyric acid to effect a resolution of the (R)-enantiomer (*Ann. de Chemie*, 20, 146 (1933)). In that situation, it was found that the (L)-methyl moiety functions as a resolving agent so that the (L)-menthyl (R)-2-hydroxy-4-phenylbutyrate can be selectively crystallized from a racemic mixture. However, this resolution requires a tedious and difficult crystallization procedure and the (R)-configured stereoisomer is isolated in low yield.

A method has now been developed whereby (R)-2-hydroxy-4-phenylbutyric acid and its esters can be prepared and isolated in an efficient, non-tedious manner by utilizing a synthetic approach involving the novel compound (L)-menthyl 2-oxo-4-phenylbutyrate.

In its composition of matter aspect, the present invention relates to the novel compounds, (L)-menthyl 2-oxo-4-phenylbutyrate, of the structural formula (2)

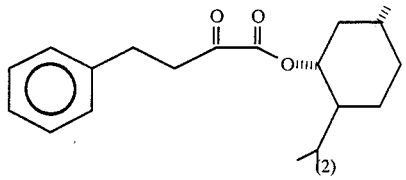

which is useful as an intermediate in the synthesis of (R)-2-hydroxy-4-phenylbutyric acid, its esters, and ACE inhibitors containing the moiety described by the structural formula (I). (L)-menthyl 2-oxo-4-phenylbutyrate (2) is prepared by condensing (L)-menthol with methyl chloroglyoxylate and reacting the resulting mixed oxalate, ethanedioic acid methyl-(L)-menthyl ester, with phenethyl magnesium bromide according to standard procedures well known in the art. The product (2) is purified and isolated by standard column chromatography and crystallization procedures.

Another aspect of the present invention relates to a novel and efficient process for the stereoselective synthesis and isolation of (R)-2-hydroxy-4-phenylbutyric acid and selected esters thereof represented by the structural formula (3)

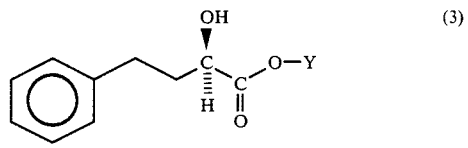

wherein Y is hydrogen, (L)-menthyl, or ($C_1$–$C_6$) alkyl. The term ($C_1$–$C_6$) alkyl contemplates an alkyl radical comprising 1 to 6 carbon atoms of straight or branched-chain configuration. The compound wherein Y is (L)-menthyl is (L)-menthyl (R)-2-hydroxy-4-phenylbutyrate represented by the structural formula (3a)

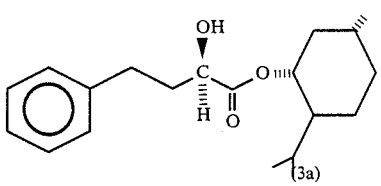

More specifically, the process aspect of the present invention relates to a stereoselective or chiral reduction of the novel compound (2) to form the corresponding (R)-configured alcohol (3a) which is hydrolyzed to its acid and re-esterified to the desired ester intermediates suitable for the preparation of ACE inhibitors. These reactions are depicted in Reaction Scheme A.

REACTION SCHEME A

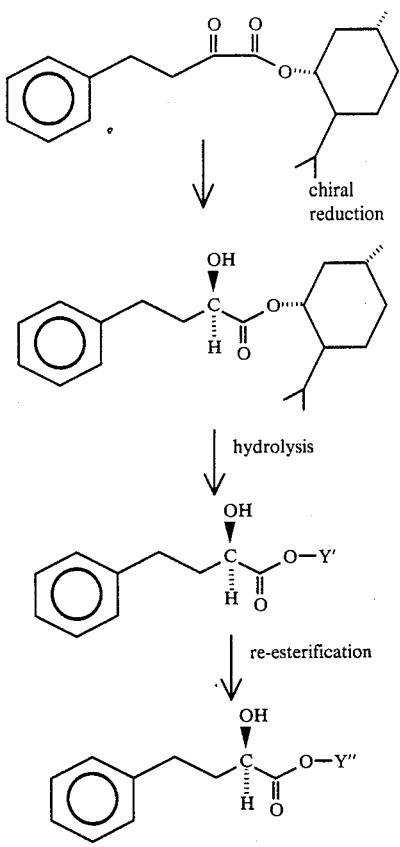

wherein Y' is hydrogen; and Y'' is (C$_1$-C$_6$) alkyl.

In effecting the above stereoselective or chiral reduction, the compound (2) is reacted with a chiral reducing agent such as S-B-(3-pinanyl)-9-borabicyclo[3.3.1]nonane. The stereo-selective reduction of non-symmetric ketones can be effected by use of a variety of chiral reducing agents. These reagents in general comprise reducing agents which favor one stereoisomer as the product of the reduction over the corresponding enantiomer. With respect to the present invention, compound (2) is subjected to a stereo-selective reduction in which the compound (3a) is favored as the reaction product over its enantiomer, by contacting (2) with S-B-(3-pinanyl)-9-borabicyclo[3,3,1]nonane or an equivalently functioning chiral reducing agent. The use of S-B-(3-pinanyl)-9-borabicyclo[3,3,1]-nonane is preferred.

Compound (2) is reacted with S-B-(3-pinanyl)-9-borabicyclo[3,3.1]nonane by contacting compound (2) and one to two equivalents of S-B-(3-pinonyl)-9-borobicyclo[3.3.1]nonane borane within the temperature range of about −20° C. to about 10° C., preferably neat or in the presence of an inert solvent, such as tetrahydrofuran (THF), diethyl ether or dimethoxyethane (DME). The reaction is generally effected over a period of 1 to 7 days. Although the reduction product so formed contains both the (R) and (S) enantiomers of the corresponding alcohol, at least 80% of the product is of the (R)-configuration, i.e., compound (3a).

The properties of the (L)-menthyl ester as a resolving agent are utilized to effect a resolution of compound (3a) from its enantiomer by standard stereo-selective crystallization techniques well known in the art. Since the chiral reduction of compound (2) results in a reduction product which is enriched in the amount of compound (3a) over that of the enantiomer, the resolution of compound (3a) proceeds more quickly and in higher yield than from a mixture of essentially equal amounts of the enantiomers. Although the (L)-menthyl ester is preferred as the resolving agent in this scheme, other equivalently functioning esters could be used which would allow a high degree of selectivity for the desired enantiomer in the chiral reduction and would function efficiently as a resolving agent in a subsequent crystallization procedure. Alternate resolving agents include (L)-8-phenyl menthyl ester and esters incorporating various N-protected (D)- or (L)- amino alcohols derived from the protection and reduction of (D)- or (L)-amino acids.

The preferred solvent for the resolution of compound (3a) from its enantiomer is a (C$_1$-C$_6$) alkanol-water mixture wherein the water comprises up to about 20% of the mixture. The term (C$_1$-C$_6$) alkanol contemplates an alkanol of 1 to 6 carbon atoms of branched or straight chain configuration or mixtures thereof such as methanol, ethanol, propanol, isopropanol and the like. A methanol-water solution is most preferred. Other solvents, however, in which the (L)-menthol ester functions as a resolving agent can also be used including non-polar solvents such as (C$_4$-C$_8$) alkanes. The term (C$_4$-C$_8$) alkane contemplates an alkane of 4 to 8 carbon atoms of branched or straight-chain configuration or mixtures thereof such as butane, pentane, hexane, heptane, octane. A temperature of about −10° C. to about 10° C. is preferred during the crystallization.

The (L)-menthyl (R)-2-hydroxy-4-phenylbutyrate (3a) synthesized and isolated by use of the present invention can be further reacted to form the corresponding (R)-2-hydroxy-4-phenylbutyric acid (3b) and C$_1$-C$_6$ alkyl esters thereof (3c) including ethyl (R)-2-hydroxy-4-phenylbutyrate.

Compound (3b) is formed by hydrolyzing compound (3a) with a Lewis base according to standard procedures well known in the art. The preferred reagent for this reaction is LiOH although many other similarly functioning bases could be used, such as NaOH, KOH or K$_2$CO$_3$.

The compound (3b) is esterified with the appropriate alcohol to form a (C$_1$-C$_6$) alkyl ester (3c) by standard procedures well known in the art. The ethyl ester is most preferred. It is preferred to effect the esterification by contacting compound (3b) with the appropriate (C$_1$-C$_6$) alkanol in the presence of an acid catalyst. For example, ethyl (R)-2-hydroxy-4-phenylbutyrate is formed by reacting compound (3b) with ethanol in the presence of an acid, preferably HCl.

Various compounds which possess activity as ACE inhibitors and hypertensive agents are prepared by reacting the trifluoromethanesulfonic ester of compounds of the formula (3c) with appropriate amines under standard conditions well known in the art which are calculated to effect an S$_N$2 displacement of the (R)-triflate by the amine. Esters of N-substituted-(S)-2-amino-4-phenylbutyric acid are thus formed which are hydrolyzed to the acids if desired.

The following examples serve to illustrate the process aspects of this invention. All temperatures are given in degrees Celsius.

EXAMPLE 1

Preparation (L)-Menthyl 2-oxo-4-phenylbutyrate
Step A: Ethanedioic acid methyl-(L)-menthyl ester A solution of 78.14 grams (g) (500 mmoles (mmol)) of (L)-menthol in 450 ml 2:1 methylene chloride-pyridine is cooled to 0° C. To this solution is added a solution of 48.9 ml (530 mmol) methyl chloroglyoxalate in 100 ml methylene chloride in a dropwise fashion. The mixture is allowed to stir overnight while warming to ambient temperature. The mixture is filtered and the precipitate is washed with ethyl acetate. The filtrate is concentrated in vacuo, taken up in hexane and refiltered. The filtrate is concentrated and distilled at 95° C. and 0.01 mm Hg using a Kugelrohr apparatus. The distilled material contains a crystalline solid which is filtered off and discarded, leaving 117.9 g analytically pure mixed ethanedioic acid methyl-(L)-menthyl ester in a yield of 97.3%. The physical characteristics of the product include:

$[\alpha]_D^{AMB}= +77.6°(c=1.2,CHCl_3)$. $^1$HNMR (300MHz): 0.79 (d, 3H, J=7.2 Hz); 0.91 (d, 3H, J=6.8 Hz); 0.93 (d, 3H, J=6.6 Hz); 0.85–1.21 (complex, 3H); 1.54 (td, 2H, $J_a$=11.5 Hz, $J_b$=3.1 Hz); 1.72 (complex doublet, J=11.6 Hz); 1.90 (septet of doublet, 1H, $J_a$=7.0 Hz, $J_b$=2.7 Hz); 2.05 (complex doublet, 1H, J=11.7 Hz); 3.90 (s, 3H); 4.86 (td, 1H, $J_a$ =10.9 Hz, $J_b$=4.5Hz). IR (film): 2950, 2920, 2870, 1770, 1740, 1460, 1320, 1200, 1170, 1150, 950 cm$^{-1}$. Anal. calcd. for $C_{13}H_{22}O_4$: C=64.44%; H=9.15%. Found: C=64.09%; H=8.98%.

Step B: (L)-Menthyl 2-oxo-4-phenylbutyrate

A freshly prepared solution of phenethyl magnesium bromide (100 mmol) is added dropwise to 24.2 g (100 mmol) ethanedioic acid methyl-(L)-menthyl ester in 40 ml dry THF while maintaining a reaction temperature of −20° C. to −25° C. (The dropping funnel is warmed slightly during the addition to keep the phenethyl magnesium bromide in solution.) The addition requires a total of 45 min. After the phenethyl magnesium bromide is added the mixture is allowed to stir 30 min. while warming to ambient temperature. To this mixture is carefully added 100 ml 1 N HCl, 100 ml ethyl acetate and 20 ml brine in succession. The organic layer is separated and washed in succession with 50 ml 1N HCl, 10 ml brine, 50 ml saturated NaHCO$_3$, and 50 ml brine. The organic solution is dried over MgSO$_4$, filtered, and concentrated in vacuo. The yellow oily residue is diluted to 100 ml with hexane, cooled to −30° C., then seeded with crystals of (L)-menthyl 2-oxo-4-phenylbutyrate. After crystallization starts, the mixture is maintained at −20° C. over night. Crystals are collected and dried to yield 12.1 g (38.3%) (L)-menthyl 2-oxo-4-phenylbutyrate. The mother liquors are concentrated in vacuo and chromatographed over silica on a 30 mm column eluting with 3% ethylacetate/hexane. The desired fractions are combined, concentrated and crystallized as above to yield an additional 2.0 g (11%) analytically pure product. The physical characteristics of the product include: melting point (m.p.)=51°–53° C. $[\alpha]_D^{AMB}= -66.4°(c=1.1, CHCl_3)$. $^1$H NMR (300 MHz): 0.75 (d, 3H, J=7.2 Hz); 0.89 (d, 3H, J =7.5 Hz); 0.92 (d, 3H, J=7.2 Hz); 0.87–1.16 (complex, 3H); 1.51 (complex triplet, 2H, J=10.4 Hz); 1.70 (complex doublet, 2H, J=11.0 HZ); 1.84 (pentet of doublets, 1H, $J_a$ =7.0 Hz, $J_b$ =2.8 Hz); 2.03 (complex doublet, 1H, J=11.4 Hz); 2.95 (t, 2H, J=7.5 Hz); 3.16 (t,2H, J=7.5 Hz); 4.81 (td, 1H, $J_a$ =11.0 Hz, $J_b$ =4.6 Hz); 7.17–7.25 (aromatic, 5H). IR (KBr): 2960, 2930, 2870, 1725, 1460, 1260, 1070, 700 cm-1. Anal. calcd. for $C_{20}H_{28}O_3$: C=75.91%; H=8.92%. Found: C=75.63%; H=8.99%.

EXAMPLE 2

(L)-Menthyl (R)-2-hydroxy-4-phenylbutyrate

A solution of 160 ml (80 mmol) 0.5 M S-B-(3-pinanyl)9-borabicyclo[3,3,1]nonane in tetrahydrofuran (THF) is concentrated to 60 ml at 30° C./120 mm Hg. The flask containing the S-B-[3-pinanyl)9-borabicyclo[3,3,1]nonane is purged with N$_2$ and cooled to −20° C. To the cooled solution is added 17.9 g (56.5 mmol) pulverized (L)-menthyl 2-oxo-4-phenylbutyrate all at once. The mixture is stirred vigorously for 1 hour (h) at −20° C. to dissolve the keto ester. The resultant solution is allowed to stand at 0° C. for 5 days. Twenty (20) ml acetaldehyde is added and the mixture is stirred 1 h while warming to ambient temperature. Volatiles are removed in vacuo and the residue is subjected to distillation conditions (70° C./1 mm Hg) for 1 hour using a Kugelrohr apparatus. The undistilled oil is dissolved in 100 ml diethyl ether and 4.8 ml (80 mmol) ethanolamine is added dropwise causing the solution to boil. A precipitate is formed immediately. The mixture is allowed to stir 10 min and is filtered through 75 ml of flash silica. The silica is eluted with 150 ml additional diethyl ether and the eluant is concentrated in vacuo to an oil which crystallizes almost immediately. The crystalline solid is dissolved in 150 ml hexane, concentrated to 75 ml, and seeded with crude (L)-menthyl (R)-2-hydroxy-4-phenyl-butyrate. The seeded mixture is cooled to −20° C. overnight. The resultant crystals are filtered and dried to yield 11.2 g of (L)-menthyl (R)-2-hydroxy-4-phenylbutyrate in a 62.3% yield. The physical characteristics of the product include: m.p.=85−86° C. $[\alpha]_D^{AMB}= -63.1°(c=0.85, CHCl_3)$. $^1$H NMR 300 MHz): 0.77 (d, 3H, J=6.67 Hz); 0.908 (d, 3H, J=8.25 Hz); 0.913 (d, 3H, J=5.70 Hz); 0.80–1.14 (complex, 3H); 1.38–1.58 (complex, 2H); 1.68 (broad s, 1H);1.72 (broad s, 1H); 1.84–2.18 (complex, 4H); 2.68 (ddd, 1H, $J_a$ =14.49 Hz, $J_b$ =10.85 Hz, $H_c$ =4.88 Hz); 2.80 (ddd, 1H, $J_a$ =14.49 Hz, $J_b$ =10.96 Hz, $J_c$ =7.05 Hz); 2.92 (d, 1H, J=5.30 Hz); 4.17 (ddd, 1H, $J_a$ =7.72 Hz, $J_b$ =5.98 Hz, $J_c$ =4.55 Hz); 4.79 (td, 1H, $J_a$ = 10.58 H$_z$, $J_6$ =4.39 H$_2$); 7.18–7.33(aromatic, 5H). IR(KBr) 3450, 2950, 2920, 2860, 1725, 1500, 1450, 1220, 1180, 1100, 690, cm-1. Anal. calcd. for $C_{20}H_{30}O_3$: C=75.46%; H =9.50%. Found: C=75.13%; H=9.59%.

In like manner, a stereoselective crystallization of (L)-menthyl (R)-2-hydroxy-4-phenylbutyrate is also effected by using methanol-water as the solvent wherein the water component comprises up to about 20% of the solvent.

EXAMPLE 3

(R)-2-hydroxy-4-phenylbutyrate

To a solution of 3.18 g (10.0 mmoles) of (L)-menthyl (R)-2-hydroxy-4-phenylbutyrate in 60 ml ethanol is added 12.5 ml (12.5 mmoles) of 1M LiOH and the mixture is warmed to dissolve the resulting precipitate. The mixture is stirred at ambient temperature overnight under a nitrogen atmosphere resulting in a precipitate being formed which does not dissolve on warming. To the mixture is added 20 ml H$_2$O which dissolves the precipitate and the ethanol is removed in vacuo. The aqueous residue is washed with two 50 ml portions of diethyl ether, acidified and extracted with three 30 ml portions of methylene chloride. The extracts are combined, dried over anhydrous MgSO₄, filtered, and concentrated in vacuo. The residue is vacuum dried and dissolved in 50 ml dry ethanol. The solution is saturated with gaseous HCl and allowed to stand at ambient temperature overnight. The solution is concentrated in vacuo and partitioned between ethyl acetate and saturated NaHCO₃. The organic layer is washed with brine, dried over anhydrous MgSO₄ and concentrated in vacuo. The residue is distilled at 120° C./1 mm Hg using a Kugelrohr apparatus which yields 1.60 g of ethyl (R)-2-hydroxy-4-phenylbutyrate in a 76.0% yield. The physical characteristics of the product include: $[\alpha]_D^{AMB} = -19.4°$ (c=1.4, CHCl₃). Anal. Calcd. for $C_{12}H_{16}O_3$: C=69.20%; H=7.68%. Found: C=69.11%; H=7.75%.

It is understood that the foregoing detailed description is given merely by way of illustration and that modifications may be made therein without departing from the spirit or scope of the present invention.

We claim:

1. The compound (L)-menthyl 2-oxo-4-phenylbutyrate.

2. In a process for making and isolating a substantially pure compound of the structural formula

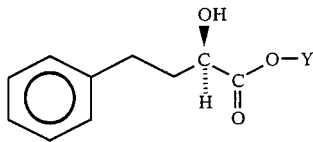

wherein Y is hydrogen or (L)-menthyl, the improvement which comprises:
   (a) stereoselectively reducing (L)-menthyl 2-oxo-4-phenylbutyrate by contacting said compound with S-B-(3-penanyl)-9borabicyclo[3.3.1]nonane
   (b) stereoselectively isolating (L)-menthyl (R)-2-hydroxy-4-phenylbutyrate by crystallization, and optionally hydrolyzing the so obtained ester.

3. A process of claim 2 wherein Y is (L)-menthyl.

4. A process of claim 2 wherein Y is hydrogen.

5. A process of claim 2 wherein the so-obtained (R)-2-hydroxy-4-phenylbutyric acid is esterified to a $C_1$–$C_6$ alkyl ester by contacting said compound with the appropriate $C_1$–$C_6$ alkanol in the presence of acid.

6. A process of claim 5 wherein (R)-2-hydroxy-4-phenylbutyric acid is converted to ethyl (R)-2-hydroxy-4-phenylbutyrate.

7. A process of claim 3 wherein the (L)-menthyl (R)-2-hydroxy-4-phenylbutyrate is stereoselectively isolated by crystallization from a solvent comprising a $C_1$–$C_6$ alkanol-water mixture wherein the water component comprises up to about 20% of the solvent.

8. A process of claim 3 wherein the (L)-menthyl (R)-2-hydroxy-4-phenylbutyrate is stereoselectively isolated by crystallization from a $C_4$–$C_8$ alkane.

9. A process for making (L)-menthyl 2-oxo-4-phenylbutyrate which comprises reacting ethanedioic acid methyl-(L)-menthyl ester with phenethyl magnesium bromide.

* * * * *